Figure 1:
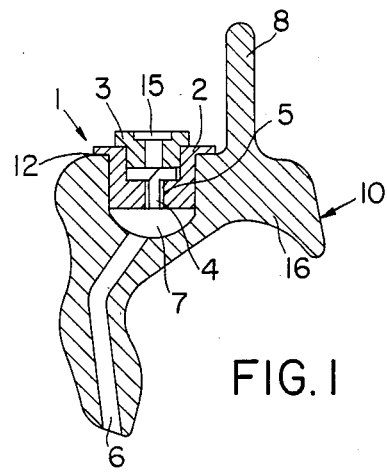

United States Patent [19]

de Boer et al.

[11] Patent Number: 4,587,965
[45] Date of Patent: May 13, 1986

[54] EAR PROTECTOR FOR KEEPING DOWN SOUND AND ASSOCIATED FILTER

[76] Inventors: Berend de Boer, Schweitzerlaan 32, 5644 DL Eindhoven, Netherlands, 5644 DL; Karel J. Doorduin, Heuvelstraat, Dongen, Netherlands, 5101 TC

[21] Appl. No.: 564,676

[22] Filed: Dec. 23, 1983

[30] Foreign Application Priority Data

Dec. 24, 1982 [NL] Netherlands ............... 8204984

[51] Int. Cl.⁴ .................................. A61F 11/02
[52] U.S. Cl. ........................................ 128/152
[58] Field of Search ....................... 128/151, 152

[56] References Cited

U.S. PATENT DOCUMENTS 2,881,759  4/1959  Hocks et al. .................. 128/152
4,353,364  10/1982 Woods ........................... 128/152

Primary Examiner—Mark L. Bell
Attorney, Agent, or Firm—Spensley Horn Jubas & Lubitz

[57] ABSTRACT

An ear protector for keeping down sound in a personalized form by causing the insertion part to match the concha part of the auricle with an appendix that can open out in the auditory canal, said ear protector having a relatively wide duct, the widened part of which receives a sound damping filter having a bore whereby the sound damping filter is arranged with satisfactory fit in the widened part of the duct, while an elongate object is placed in the bore of the filter so that a free passage in the bore remains possible with a maximum difference in distance between the outer side of the elongate object and the inner side of the bore of 0.33 mm at the narrowest passage.

12 Claims, 7 Drawing Figures

EAR PROTECTOR FOR KEEPING DOWN SOUND AND ASSOCIATED FILTER

The invention relates to an ear protector, for keeping down sound, in a personalized form by causing the inserting part to match the concha part of the auricle with an appendix that can open out in the auditory canal, said ear protector having a relatively wide duct having in its widened part a sound reducing filter having a bore.

Such an ear protector is known from U.S. Pat. No. 2,881,759, in which the filter is slidably arranged in a widened part of the duct, the displacement of the filter producing a higher or lower sound damping effect. This patent does not indicate numbers relating to the diameter of the duct through the ear protector. In practice it has been found to be an inconvenience for the user of the ear protector to have to displace the filter. It is, moreover, a disadvantage that the filter protruding from the ear protector can be slipped inwards when touched so that the ear protector then operates as a fully closing ear plug.

From a publication of the Dutch Labour Inspection 1975 P 138 it appears that attempts have to be made to restrict sound nuisance as much as possible by taking technical precautions so that the sound level in workshops is reduced to an acceptable value and, if it is not possible to ensure acceptable sound levels, ear protectors have to be used.

The best known ear protectors are: (a) ear flaps, (b) ear plugs and (c) glass-down paddings.

In industry ear flaps are often used because they can be satisfactorily combined with a safety cap or a safety helmet, whilst the ear flaps provide a reasonable sound reduction. However, a disadvantage of ear flaps is that the user feels much troubled by them at relatively high temperature, for example, in summer or in a workshop having relatively high temperatures. Moreover, the ear flap is impersonal, which may give rise to undesirable hygienic conditions. At higher temperatures perspiration may accumulate in the ear flap giving rise to all kinds of undesirable hygienic disadvantages. For these reasons an ear flap is often left aside though sound nuisance is prevailing in the working room.

Glass-down padding is cheap and suitable for use only once, so that the hygienic disadvantages of ear flaps are not involved here. Moreover, the padding can be used more easily at higher temperatures, but these glass-down paddings have given rise several times to ear infections due to penetration of glass fibres into the auditory canal. If the glass-down padding is not sufficiently firmly placed in the ears, there is no protection. Furthermore plugs of a deformable synthetic resin are known, which can be placed in the ear after being kneaded. However, it is difficult to give the ear plug the correct shape. When the ear plug does not have an optimum shape, too much sound will penetrate alongside thereof, so that adequate protection against sound nuisance is not obtained. The effect of such ear plugs can then be compared with that of ordinary cotton-wool which, in contrast to glass-down padding, does practically not protect against noise. A further disadvantage of glass-down paddings, known ear plugs and ear flaps is that in the case of complete closure the ear is completely cut off from the surroundings so that any communication becomes difficult and sound orientation is drastically reduced, which may be particularly important in warning those carrying the ear protecting means in the event of hazards. Complete closure of the ears is generally felt to be very disagreeable.

In order to avoid the aforesaid disadvantages ear protectors have been developed of the kind disclosed in U.S. Pat. No. 2,881.759, in which a duct is passed through the ear protector so that an open communication is maintained between the interior of the auditory canal and the surroundings. This duct prevents the user from feeling cut off, whilst communication with the surroundings remains possible, but the sound reducing effect is excessively reduced because it is structurally very difficult to provide such a small duct in the filter that a satisfactory sound damping effect is obtained. Therefore structurally more complicated ear protectors have been developed as described in the aforesaid U.S. Pat. No. 2,881,759 or as disclosed in U.S. Pat. No. 4,353,364, where it is possible to provide a relatively wide duct in the ear protector, said duct being narrowed by a controlmember in the duct.

The research made has proved that with a given maximum bore in the filter a satisfactory sound reducing effect can be obtained, whilst communication with the ambience remains possible. The ear protector according to the invention is characterized in that the sound reducing filter is satisfactorily fitting in the widened part of the duct, whilst an elongate object is placed in the bore of the filter so that a free passage remains possible in the bore with a maximum difference in distance between the outer side of the elongate object and the inner side of the bore of 0.33 mm at the narrowest passage.

The ear protector according to the invention can thus be readily constructed because a bore can be made in the filter in a conventional manner, said bore being narrowed by introducing an elongate object into the bore so that the bore is narrowed. The damping effect is also determined by the length of the bore in the filter. A preferred filter length is 5 mm and the length of the bore with limited passage is about 3 mm.

As far as the bore in the filter is concerned, it will be obvious that the smaller is the passage the better will be the sound reducing effect, whereas the passage has to be sufficiently large to maintain an air flow. In practice it has been found to be difficult to provide a bore of sufficient length and a diameter of less than 0.30 mm. Therefore, in the ear protector according to the invention a filter is used which readily allows making a bore of, for example, 0.33 mm or more, whilst an elongate object is placed in the bore, the diameter of which is such that the remaining passage ensures the desired sound damping effect.

The elongate object is preferably a wire, but it may have any desirable other shape.

The invention furthermore relates to the filter used in the ear protector embodying the invention.

Figure 4:
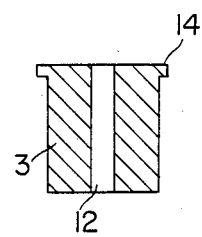
Figure 2:
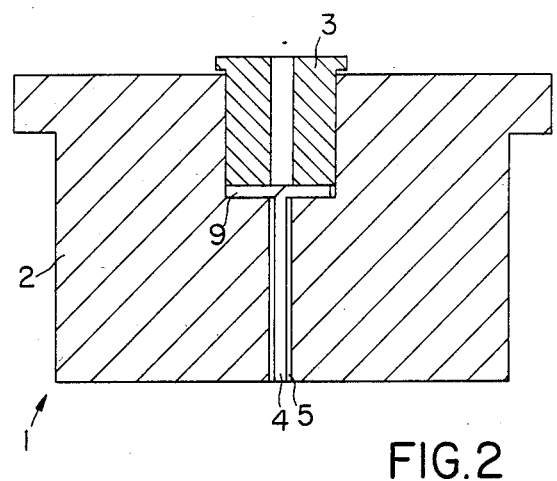
Figure 3:
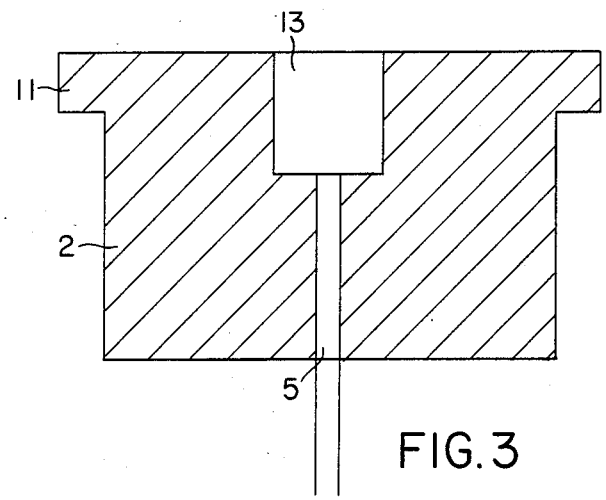
Figure 5:
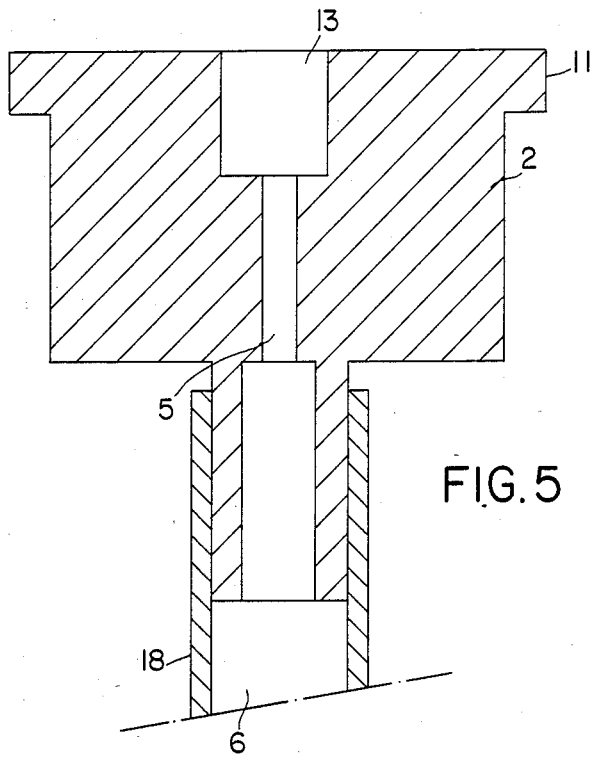
Figure 6:
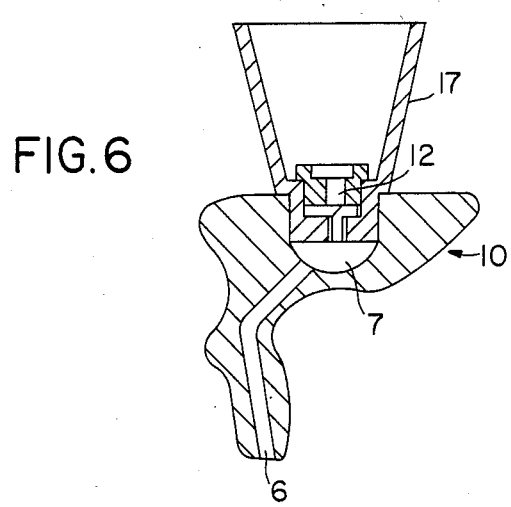
Figure 7:
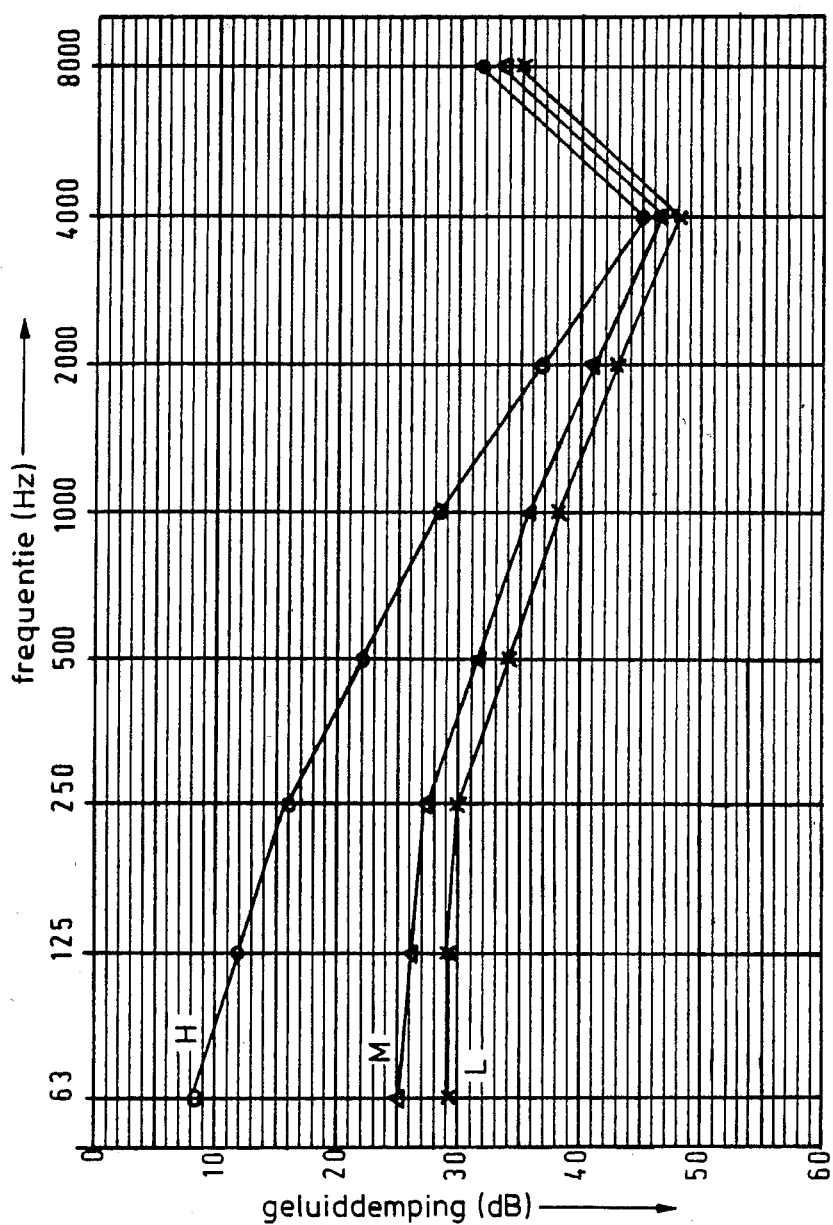

The invention will be further described with reference to the accompanying drawing, in which FIG. 1 shows the ear protector with a filter in accordance with the invention, FIG. 2 shows the filter, FIG. 3 shows the fitting piece of the filter, FIG. 4 shows the insertion piece of the filter, FIG. 5 shows the fitting piece in an alternative embodiment to be arranged in an ear protector holder of relatively soft material, FIG. 6 shows an alternative embodiment of the ear protector of FIG. 1 and FIG. 7 is a graph of the sound damping effect by three filters in dependence on the sound frequency.

FIG. 1 shows an ear protector embodying the invention, which is presonalized by its specific shape. The ear protector has a duct 6 opening out in a widened part 7 in which the filter 1 is arranged. This filter comprises a fitting piece 2 having a bore 5, in which an insertion piece 3 is arranged, which ensures that the elongate object, preferably a wire 4, is held in place in the bore 5. The ear protector is furthermore provided with a grip 8 by which the ear protector can be readily put into the ear or removed therefrom. The ear protector holder 16 i.e. the ear protector 10 without filter 1 may be made from a relatively rigid material, for example, a polyacrylate, which material has the advantage that ducts can be easily made therein. The manufacture of a personalized ear protector according to the invention from a hard material is, however, time-consuming because in this case at first a print has to be made of the inner part of the ear of the potential user of the ear protector. By means of this mould the final ear protector is made. As an alternative, the ear protector can be made from a relatively soft material, for example, silicon, in which case the relatively soft material can assume the desired shape of the concha of the auricle in a single operation. Because it is more difficult to make ducts in a relatively soft material with the desired diameter, a fitting piece 2 of the kind shown in FIG. 5 has been developed, which will be explained hereinafter. FIG. 2 shows a filter 1 embodying the invention which comprises a fitting piece 2 in which an insertion piece 3 is arranged. The bore 5 is made in the fitting piece 2 and prolonges in the insertion piece 3. An elongate object, preferably a wire 4 is arranged in part of the bore 5 or in the whole bore 5 so that a part of the bore 5 has a considerably smaller free flow passage. FIG. 3 separately shows the fitting piece 2 and FIG. 4 shows the insertion piece 3. The fitting piece 2 has a cavity 13 for the insertion piece and a collar 11, which may protrude by a height of about 1 mm above the ear protector holder 16. The overall height of the fitting piece 2 is about 5 mm and the diameter is about 7.5 mm. The bore 5 has a diameter depending on the diameter of the elongate object 4, whilst the free passage between the object and the bore 5 will be 0.33 mm at the most. Preferably the diameter of the bore is 0.3 to 0.5 mm. The insertion piece 3 has a bore 12 and a collar 14. The width of the insertion piece 3 is preferably 1.7 mm and the height is preferably 2.2 mm, whilst the height of the collar 14 is about 0.25 mm. The bore 12 in the insertion piece is preferably equal to the bore 5 in the fitting piece 2. By introducing the elongate object such as the wire 4 into the bore 5 as shown in FIG. 2 the effective passage of the bore is appreciably reduced. By choosing the diameter of the wire 4 various types of filters can be obtained, that is to say, an M filter having a wire of a diameter of 0.2 mm and an L filter having a wire of a diameter of 0.25 mm in a bore 5 of 0.33 mm.

The results obtained by these M and L filters are shown in FIG. 7.

Comparing the insertion piece 3 of FIG. 4 with that of FIG. 1 it will be seen that there is a difference on the top side of the insertion piece 3, the bore of FIG. 1 opening out in a larger open cavity 15 serving to avoid clogging of the bore 12. When the ear protector is introduced, the filter 1 may be touched near the end of bore 12 in the insertion piece 3 so that grease or dust particles on the finger may cause clogging of the bore 12. It is, therefore, preferred to have the bore 12 opening out in a larger cavity 15 as shown in FIG. 1. It is also possible to provide the bore 12 with a screening hook or the like so that penetration of dirt is effectively avoided, but such constructions render the ear protector more expensive, though such embodiments are lying within the scope of the invention.

FIG. 5 shows an embodiment of a fitting piece 2 for an ear protector holder of relatively soft material, the fitting piece 2 being provided with a flexible tube 18, inserted into the material of the ear protector holder before it is adapted to the person concerned. By providing the tube on the fitting piece 2 later problems are avoided, when the ear protector holder has been made to fit and had to be bored to form the duct 6, because the bore is already obtained by means of the tube.

FIG. 6 shows an alternative embodiment of the ear protector of FIG. 1, in which grip 8 and filter 1 are combined to form a holding member 17, in which the grip 8 coincides with the filter 1. An additional advantage of the ear protector of FIG. 6 is that penetration of dirt into the bore 12 can even be more avoided than in the embodiment of FIG. 1, whilst the filter may have a greater length without protruding in a troublesome manner. The lengthening of the filter, especially of the bore of restricted passage has the advantage that the bore may be wider in order to obtain uniform damping in accordance with the formula $D = k \cdot (l/O)$, wherein D = damping
l = length of bore
O = surface of bore and
k = fixed factor (at a given frequency).

Apart from the insertion of the elongate object 4 into the bore 5, a ceramic or glass plate having very fine pores may be arranged in the cavity 9 of FIG. 2. The free passage in the bore with the wire could be expressed as a surface size, although the size depends on the diameter of the bore. A preferred surface of the passage is 0.005 to 0.1 mm$^2$.

The wire 4 may be made of stainless steel, copper, yarn or a synthetic resin, for example, Nylon.

FIG. 7 indicates the result of measurements in accordance with ISO 4869 with sound reducing filters M and L embodying the invention. In FIG. 7 curve "H" relates to a filter without wire in bore 5, which had a diameter of 0.33 mm. From the results indicated by the curves of FIG. 7 it appears that an improvement of the damping is obtained by using an ear protector according to the invention.

The advantages obtainable by the ear protectors according to the invention are that they are satisfatorily fitting, are light of weight and do not press against the edge of the auditory canal. Furthermore they can be readily placed in and removed from the ear, whilst these ear protectors do not cause sensation of being closed in and the notion of direction remains intact.

The figures used in the claims are only meant to explain more clearly the intention of the invention and are not supposed to the only restriction concerning the interpretation of the invention.

We claim:

1. An ear protector for insertion in the concha of an ear comprising:
   a protector body sized to fit securely within the concha and having a duct therethrough for permitting transmission of sound through the body;
   a filter within a portion of the duct for reducing the sound transmission through the duct wherein the filter has a bore therethrough;

an elongated member within at least a portion of the filter bore for further reducing sound transmission through the duct.

2. The ear protector of claim 1 further comprising a perforated plate within a portion of the filter bore.

3. The ear protector of claim 1 wherein the protector body is moulded to conform to the shape of a particular person's cochlea.

4. The ear protector of claim 1 wherein the body duct includes a first portion larger than a second portion and the filter is sized to fit securely in the first portion.

5. The ear protector of claim 4 wherein the elongated member extends through both portions of the body duct and wherein the duct and the elongated member are sized to leave a passageway for sound transmission through the body, the passageway having a diameter of at most about 0.33 mm.

6. The ear protector of claim 1 wherein the length of the filter bore is about one-half the depth of the cochlea.

7. The ear protector of claim 1 wherein the elongated member is a metal wire.

8. The ear protector of claim 1 wherein the elongated member is formed of a synthetic resin.

9. The ear protector of claim 2 wherein the perforated plate is ceramic.

10. The ear protector of claim 2 wherein the perforated plate is glass.

11. The ear protector of claim 7 wherein the wire has a diameter of about 0.3 mm.

12. The ear protector of claim 1 further comprising means secured to the filter and extending beyond the protector body for inserting the protector in an ear.

* * * * *